United States Patent
Sweitzer et al.

(10) Patent No.: US 6,954,664 B2
(45) Date of Patent: Oct. 11, 2005

(54) OXIMETRY SIMULATOR

(75) Inventors: Robert Lee Sweitzer, Milwaukee, WI (US); Eugene Palatnik, Pewaukee, WI (US)

(73) Assignee: Smiths Medical PM, Inc., Waukesha, WI (US)

( * ) Notice: Subject to any disclaimer, the term of this patent is extended or adjusted under 35 U.S.C. 154(b) by 78 days.

(21) Appl. No.: 10/465,888

(22) Filed: Jun. 20, 2003

(65) Prior Publication Data

US 2004/0260160 A1 Dec. 23, 2004

(51) Int. Cl.$^7$ ................................................. A61B 5/00
(52) U.S. Cl. ......................................... 600/323; 128/903
(58) Field of Search ................................. 600/310, 322, 600/323, 333; 128/903

(56) References Cited

U.S. PATENT DOCUMENTS

| | | | | |
|---|---|---|---|---|
| 5,323,776 A | * | 6/1994 | Blakeley et al. | 600/324 |
| 5,784,151 A | * | 7/1998 | Miller et al. | 600/330 |
| 5,830,137 A | * | 11/1998 | Scharf | 600/323 |
| 5,964,701 A | | 10/1999 | Asada et al. | |
| 6,584,336 B1 | * | 6/2003 | Ali et al. | 600/323 |

* cited by examiner

*Primary Examiner*—Eric F. Winakur
(74) *Attorney, Agent, or Firm*—Louis Woo

(57) ABSTRACT

A simulator adapter is provided to be used with a conventional oximeter for monitoring a patient who may be remotely located from the oximeter. In a first embodiment of the invention, the simulator adapter has a simulator digit that fits to the sensor of the oximeter. The simulator digit senses the light output from the oximeter and provides a feedback to the simulator adapter to enable the adapter to adapt the signal of the patient sent to the adapter for use by the oximeter, as if the patient is on-site and is being measured by the oximeter. In a second embodiment, in place of a simulator digit, the simulator adapter has as its output a connector which is adapted to mate with the conventional connector that is part of the conventional oximeter. This second embodiment eliminates the need for any simulator digit and sensor for the oximeter, as appropriate circuitries are provided in the simulator adapter to enable it to connect directly to the oximeter. In an environment where the signal from the patient may be affected electromagnetically, the simulator adapter may be connected to the remote oximetry unit by a fiber optic cable, so that the signal representing the physiological parameter remotely measured from the patient is directly sent either to the simulator digit of the first embodiment or the adapter connector of the second embodiment.

31 Claims, 3 Drawing Sheets

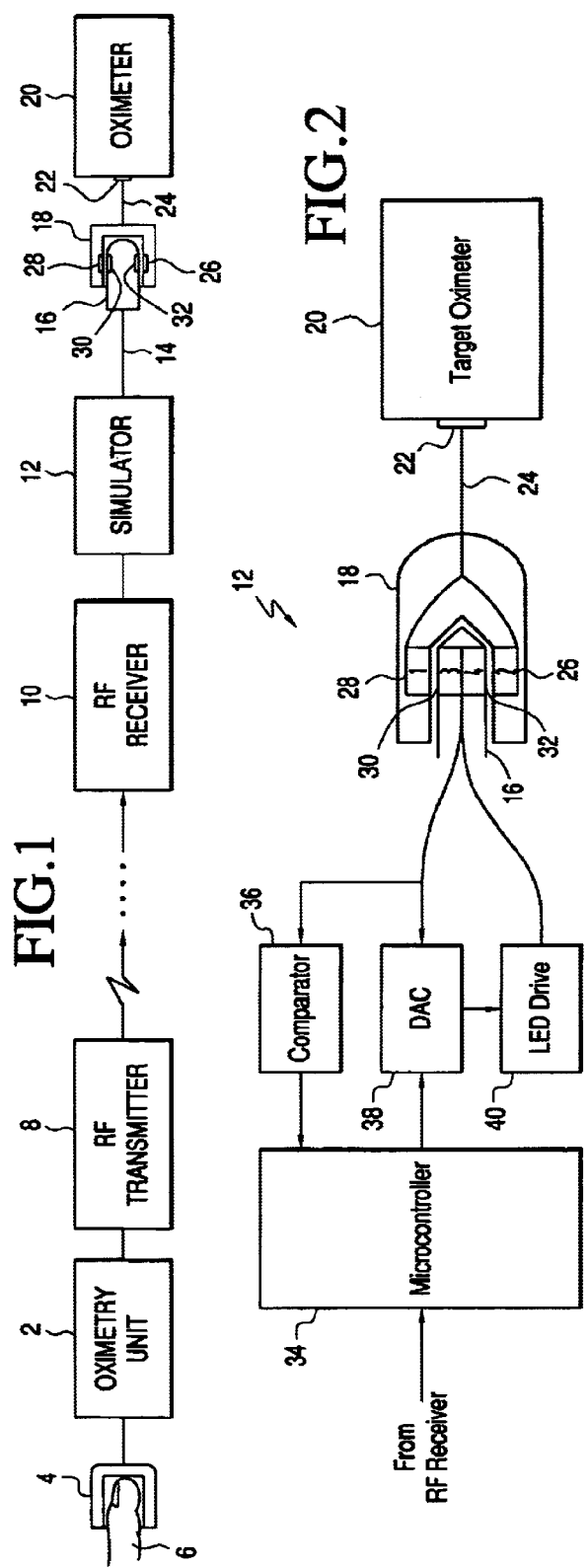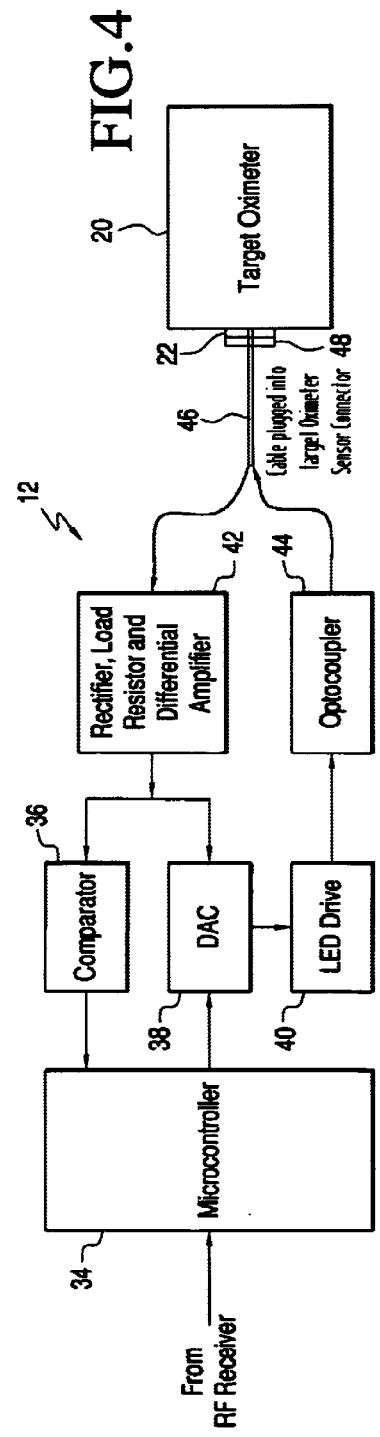

OXIMETRY SIMULATOR

FIELD OF THE INVENTION

The present invention relates to oximeters and more particularly to a simulator that is adapted to provide to a target oximeter the SpO2 data measured by a remote oximetry unit.

SUMMARY OF THE PRESENT INVENTION

Co-pending U.S. application Ser. No. 10/284,239, assigned to the same assignee as the instant application, discloses a finger oximeter with remote telecommunications capabilities. The disclosure of the '239 application is incorporated by reference to the disclosure of the instant application. The '239 application in particular discloses that the data measured by the finger oximetry unit may be transmitted to a remote device such as the Vital Signs monitor manufactured by the assignee of the instant invention which has built therein a RF receiver attuned to receive the RF signal being transmitted by the finger oximetry unit.

The present invention is directed to those conventional on-site oximeter units that are equipped with a connector, such as a conventional DB-9 connector, that has a sensor mated thereto by means of a cable. Such oximeters, prior to the instant invention, are used for measuring the blood saturation oxygen level (SpO2) of a patient by having the patient insert her finger into the sensor. Each of those on-site oximeters may have its own characteristics in that the circuitries employed by each oximeter may generate characteristics different from the other oximeters and accordingly would accommodate only a particular type of sensor.

The instant invention simulator enables a remote oximetry unit, such as for example the finger oximetry unit disclosed in the aforementioned '239 application, to take a measurement of a patient remote from a target oximeter, and by means of the simulator, effectively allows the target oximeter to read out the measured patient data from the remote oximetry unit, irrespective of the type of target oximeter being used and the particular sensor to be used with the target oximeter.

To achieve this end, the oximetry simulator of the instant invention, in a first embodiment, includes a unit that resembles the finger or digit of a patient insertable into the sensor of the on-site target oximeter. The unit has incorporated therein a photo diode and a light emitting source. The unit is configured such that when it is inserted into the sensor of the target oximeter, its photo diode is aligned in opposed relationship to the LED of the target oximeter, while its light emitting source is aligned to oppose the photo detector in the sensor of the target oximeter. The unit is connected to a simulator main module which includes therein a comparator circuit, a digital to analog circuit, a light emitter driver circuit, and a processor circuit. The light measured by the photo detector of the simulator is sent to the comparator circuit and the digital to analog conversion circuit. As the simulator receives the signal corresponding to the SpO2 measured from a patient by the remote oximetry unit, its processor circuit also takes in data from the target oximeter measured by the sensor of the simulator unit.

The received SpO2 signal is used to generate a number that corresponds to the remotely measured patient data. The number is sent to the digital to analog converter circuit. This number and the input data from the target oximeter measured by the photo detector of the simulator are used to generate an output that is fed to the light emitter driver circuit so that an appropriate amount of light is output from the light emitting source of the simulator unit to the photo detector of the sensor of the target oximeter. By thus providing a feedback, an accurate representation of the patient data remotely measured could be fed to the target oximeter, irrespective of the particular characteristics of the circuitries of the target oximeter. An accurate display or monitoring of the physiological parameters of a patient located remotely from the target oximeter is thereby accomplished.

In a second embodiment of the instant invention, in place of a simulator unit shaped like a human digit that fits to the sensor of the target oximeter, a simulator connector is directly mated to the counterpart connector of the target oximeter. The interfacing of the simulator digit and the sensor of the target oximeter is therefore eliminated. By directly connecting the simulator to the target oximeter via connectors, sensors for the target oximeters are no longer needed. Such sensors ordinarily are the most expensive part of a conventional on-site oximeter unit and require constant replacement. The elimination of such sensors accordingly substantially reduces the cost for the user of the on-site target oximeter. In addition, ambient disturbances that might occur due to the mating of the simulator digit with the sensor are eliminated. But for the simulator digit and its photo detector and LEDs, the circuitries of the simulator for the second embodiment are substantially the same as those of the first embodiment.

BRIEF DESCRIPTION OF THE FIGURES

The instant invention will become apparent and will be best understood by reference to the following description of embodiments of the invention taken in conjunction with the accompanying drawings, wherein:

FIG. 1 is an overall view of the interaction between a remote oximetry unit and the inventive simulator unit, and the interaction of the latter with an on-site or target oximeter;

FIG. 2 is a semi-block diagram illustrating a first embodiment of the instant invention;

FIG. 4 is a block diagram illustrating a second embodiment of the instant invention.

DETAILED DESCRIPTION OF THE INVENTION

Figure 3:
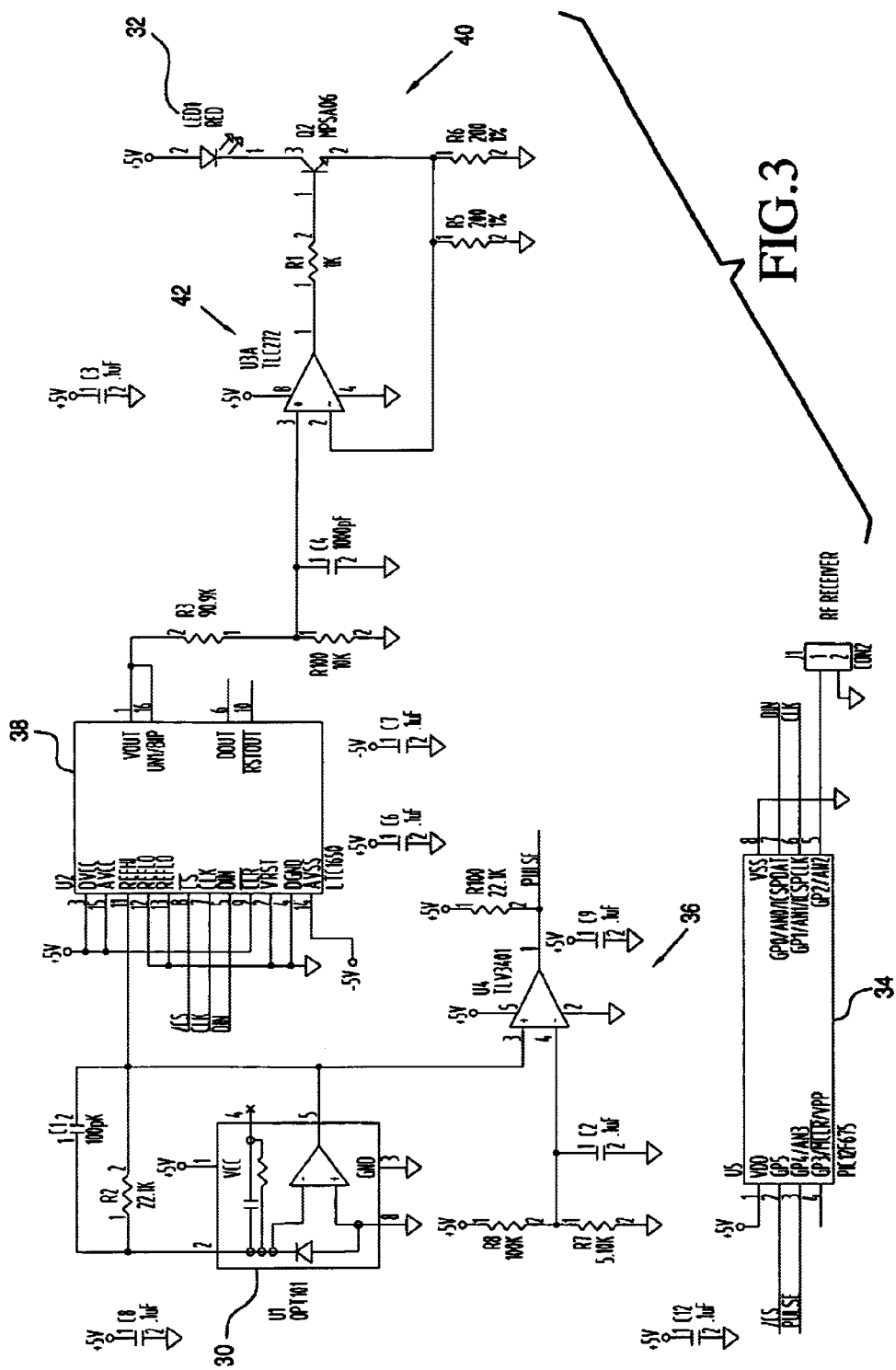
FIG. 3 is a schematic of the circuitries to be used with the embodiment of the instant invention as shown in FIG. 2.

With reference to FIG. 1, an oximetry unit 2, such as that disclosed in the aforenoted incorporated by reference '239 application, is shown to have a sensor 4 to which is inserted a digit 6 of a patient. A physiological parameter of the patient, such as for example her SpO2 (oxygen saturation of blood), is taken or measured. The measured patient parameter is routed to a RF transmitter 8 that transmits the measured data in a conventional way telecommunicatively, such as for example by RF, to a RF receiver 10 that is attuned to receive the RF signals from RF transmitter 8. Although shown as separate units, sensor 4 and RF transmitter 8 each, or both, may be part of oximetry unit 2, particularly if oximetry unit 2 is a telemetric finger oximeter such as that disclosed in the aforenoted '239 application.

RF receiver 10 is connected to, or could be a part of, a simulator unit 12. In the embodiment shown in FIG. 1, simulator 12 has connected thereto, by a cable 14, a unit 16 that is shaped like a human digit. Unit 16 is input to a sensor 18 of an on-site conventional target oximeter 20. As is well known, a conventional on-site oximeter such as oximeter 20 has a connector 22, such as a DB-9 connector, to which is mated a cable 24 of sensor 18 by means of a counterpart connector. In other words, if connector 22 of oximeter 20 were a female connector, then the connector at the end of cable 24 for sensor 18 would be a male connector, and vice versa. Sensor 18 is a conventional oximeter sensor that has a photo detector 26 and a light source such as a conventional multi waveform LED light source 28. As should be appreciated, there are a number of conventional on-site oximeters manufactured by a number of companies. And each brand of the on-site oximeters is adapted to work with a particular type of sensor. The inventive simulator is adapted to work with most, if not all, of these on-site oximeters.

FIGS. 2 and 3 provide an illustration of the various circuitries in simulator unit 12, and the interaction between those circuitries with the target oximeter, by means of the mating of the simulator digit to the sensor of the target oximeter. In particular, simulator unit 12 has a microcontroller (or a microprocessor) 34 that is interconnected with a comparator (or comparator circuit) 36 and a digital to analog converter (or digital to analog converter circuit) (DAC) 38. DAC 38 in turn is connected to a LED drive circuit 40. The simulator digit 16, as best shown in FIG. 2, has integrated to the unit a simulator photo detector 30 and a simulator LED light source 32. The simulator photo detector 30 and simulator LED 32, when simulator digit 16 is inserted into sensor 18 of the target oximeter 20, are positioned to be aligned in opposed relationship to the target oximeter light emitter 28 and the target oximeter photo detector 26, respectively. Insofar as target oximeter 20 could be any one of a plurality of conventional oximeters, the circuitries and the operation of the target oximeter 20 are not given herein, aside from the brief note that such target oximeter may include a monitor or a display that shows the blood oxygen concentration, or the SpO2, of the patient, as it is being measured.

With reference to FIGS. 2 and 3, the simulator digit 16 that is adapted to fit into sensor 18 has its simulator photo detector 30, by means of OPT-101 (U1, FIG. 3), sensing the light intensity of the light output from LED 28 of sensor 18. By sensing the intensity of the light, which is converted into a signal by means of the OPT-101 diode, simulator photo detector 30 is able to output a signal (at pin 5 in component U1 of FIG. 3) to comparator circuit 36 (pin 3 of U4) and digital to analog converter 38 (pin 11 of U2). At the same time, processor 34 is receiving from the RF receiver 10 the RF signal transmitted by oximetry unit 2 by way of its RF transmitter 8. The RF signal, which is representative of the SpO2 due to the blood flow of the patient, is input to processor 34 by way of connector CON2 as shown in FIG. 3. Alternatively, the signal may be directly fed to processor 34, if RF receiver 10 is part of simulator unit 12.

In receipt of the RF signal from the oximetry unit 2, processor 34 generates a number N that corresponds to the data represented by the signal. To illustrate, if the SpO2 of the patient being measured by the oximetry unit 2 is 98.6%, then processor 38 would generate a number N that corresponds to 98.6% SpO2 upon receipt of the RF signal. Processor 34 has a memory that has stored therein a plurality of Ns, each of which represents a given SpO2. Thus, upon receipt of the RF signal which corresponds to a given N, processor 34 retrieves the corresponding N from its memory and outputs that N, which is representative of the being measured SpO2, to DAC 38, per output line CLK at pin 6 of processor 34. If the being measured SpO2 changes, a different N is retrieved from the memory of processor 34 and fed to DAC 38 at a frequency as determined by simulator photo detector 30. The RF signal received from oximetry unit 2 may be a combination of the red and infrared waveforms that correspond to the SpO2 detected from digit 6 of the patient.

Also provided by processor 34 to DAC 38 are outputs from line DIN and /CS (leads 7 and 2 of U5). The frequency with which N is clocked into DAC 38 is dependent on the light from LED 28 of sensor 18 of target oximeter 20. This light intensity, measured by simulator photo detector 30, is fed through an amplifier (part of U1) and output therefrom (at pin 5) to comparator 36, for comparison with a reference voltage that is generated by the combination of resistors R8, R7 and capacitor C2. Comparator 38 (U4) senses the output from simulator photo detector 30 as a voltage, and outputs a pulse each time that target oximeter 20 has "fired" a red or infrared pulse, which is the pulse of light used to measure the SpO2 from a finger inserted into sensor 18. Thus, depending on the intensity of the light sensed by simulator photo detector 30 from LED 28 of target oximeter 20, pulses having a specific frequency are output from comparator 36. These pulses are fed to processor 34 (pin 3 of U5), which outputs N as a function of the timing provided by the pulses. For the embodiment at hand, it is assumed that N is output by processor 34 at 120 times per minute.

In receipt of N from processor 34 and the voltage input from simulator photo detector 30, DAC 38 calculates an output voltage based on the following formula:

$$V_{out} = V_{in} * (N/M)$$

Where $V_{out}$ and $V_{in}$ are the output and input voltages, respectively, out of and into DAC 38;
N=number that is clocked into DAC 38 by processor 34; and
M=resolution number of DAC 38 selected from $2^8$ to $2^{24}$.

Not to be limiting, for the embodiment at hand, the inventors found that a resolution of $M=2^{12}$ or 4096 provides an output voltage $V_{out}$ that works best with the DAC component for the schematic shown in FIG. 3. Note, however, that for different DACs, depending on the brand and type of DAC and other components used in the circuit, another value M within the range of values listed ($2^8$ to $2^{22}$) may have to be used.

The output voltage $V_{out}$ is provided by DAC 38 to a voltage to current converter 42 (U3A) that converts the $V_{out}$ into a current to drive the simulator LED 32, which is positioned opposed to photo detector 26 of the target oximeter 30 so that, as far as target oximeter 20 is concerned, a patient has inserted one of her digits into sensor 18, and that SpO2 is being measured from the inserted digit. For the schematic shown in FIG. 3, LED drive 40 includes voltage to current converter 42 and transistor driver Q2.

Figure 5:
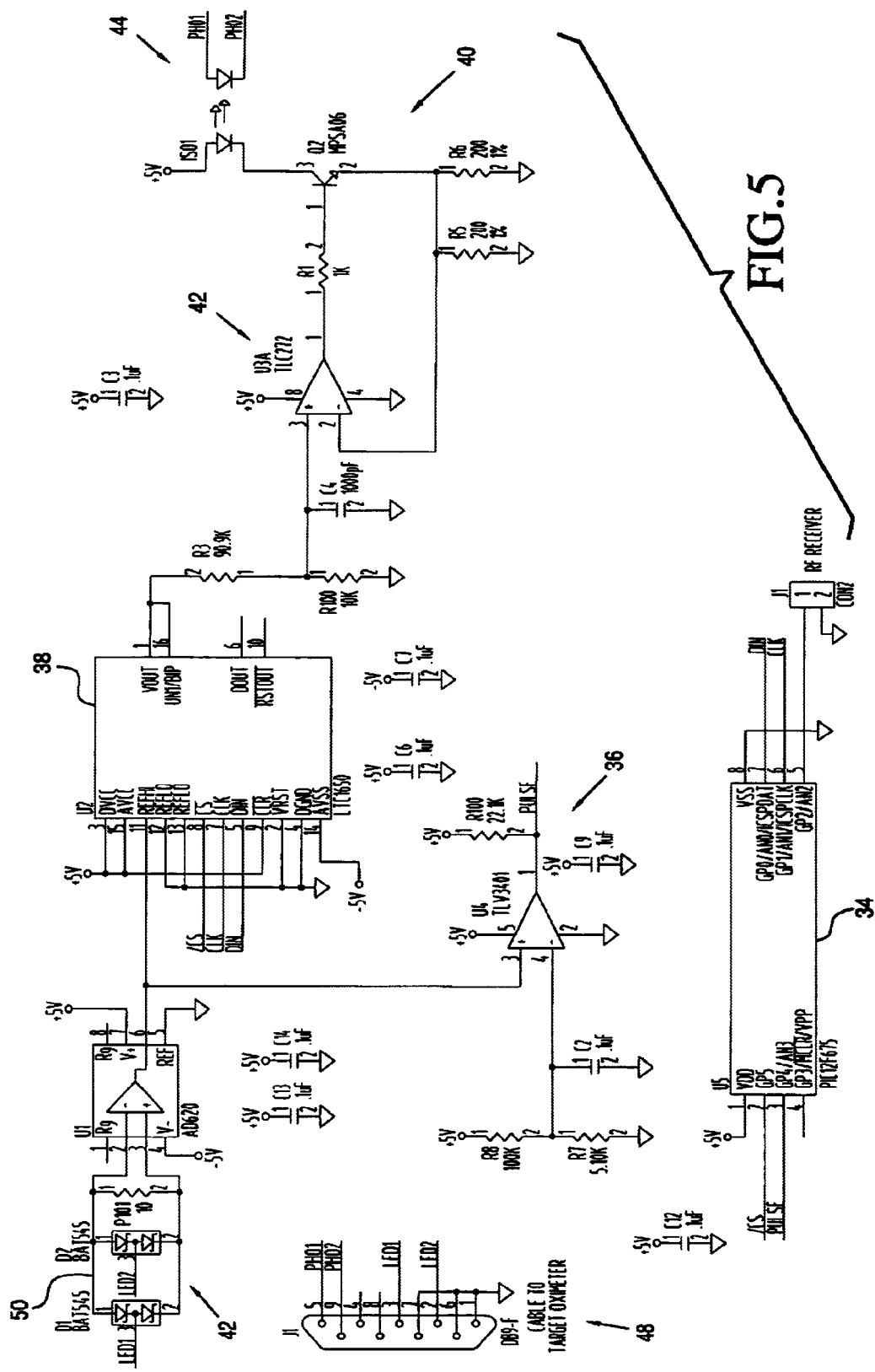
FIG. 5 is an electrical schematic of the embodiment of the instant invention as shown in FIG. 4.

A second embodiment of the instant invention is shown in FIGS. 4 and 5. The second embodiment eliminates the need for a simulator digit represented by body unit 16 that is inserted to sensor 18. Sensor 18 is also eliminated. Among the advantages for the second embodiment is the reduced cost associated with elimination of the finger digit simulator and sensor 18. Furthermore, any ambient disturbances such as aberrant light that seeps into the mated simulator digit/sensor is eliminated, insofar as the second embodiment is not affected by any ambient light. This is due to the fact that the output from the simulator unit 12 is in the form of a connector that mates to the already existing connector at the target oximeter 20 that ordinarily is used to connect to sensor 18, by way of cable 24. The same components in the second embodiment as the first are labeled the same in FIGS. 4 and 5.

With reference to FIGS. 4 and 5, the second embodiment of the instant invention is different from the first embodiment in that the simulation digit 16 and sensor 18 have been replaced by an input circuit 42 having a combination rectifier, load resistor and differential amplifier circuits and an opto-coupler 44. For the embodiment shown in FIGS. 4 and 5, the circuitries of the simulator unit 12 are connected directly to the target oximeter 20 by a cable 46. A connector 48, for example in the form of a conventional DB-9 female connector, is provided at the end of cable 46 for coupling to target oximeter 20 by mating to connector 22, assumed for this embodiment to be a male DB-9 connector.

Input circuit 42 provides an input rectifier circuit 50 built around dual diodes D1 and D2. The dual diodes D1 and D2 are connected to a load, in the form of a resistor R101. The differential amplifier U1 amplifies the signal detected by input circuit 42 from the output of target oximeter 20 which, for the first embodiment, corresponds to the intensity of light output from the LED at its senor 18. As before, the output from amplifier U1 is fed to comparator 36 and DAC circuit 38. Also, processor 34 outputs a number N, which represents the physiological parameter of the patient possibly in the form of SpO2 being measured by the remote oximetry unit, to DAC 38 in a frequency that is a function of the pulse output from comparator 36. The pulse output in turn is dependent on the signal sensed by input circuit 42 from target oximeter 20.

The output from DAC 38, which is the same voltage output from the above noted formula, is provided to voltage to current convertor 42 for controlling drive transistor Q2, which in turn controls the opto-coupler 44 (ISO1). The photo diode leads of opto-coupler 44 are routed to the DB9 connector 48, for example pins 5 and 9 of the connector (FIG. 5) for input to target oximeter 30. The LED outputs from the target oximeter for the exemplar second embodiment are routed through leads 2 and 3 of the connector (FIG. 5) when the simulator unit 12 is coupled to target oximeter 20, via the mating of connector 48 to connector 22. Note that connector 22 of the target oximeter 20 is the connector to which cable 24 of the conventional finger sensor 18 is plugged into, when oximeter 20 is used prior to the instant invention, and also with respect to the first embodiment.

With respect to both embodiments of the instant invention as disclosed above, a simulator may be adapted to enable a conventional oximeter, which ordinarily requires that a patient be present in order to measure her blood oxygen concentration level, to measure the SpO2 of a patient who may be located remotely from the oximeter. Moreover, patient cables and finger sensors which are relatively expensive and require constant replacement are no longer needed. Furthermore, when a telemetric finger oximeter such as that disclosed in co-pending '239 application is used, a conventional oximeter that has multiple inputs and displays may be used to monitor a plurality of patients each of whom may be located at a different location.

In an electrical or magnetic interference environment, as for example where the patient is in a room for MRI (Magnetic Resonance Imaging) scanning and the SpO2 of the patient is desired, a telemetry unit would not work since telemetry signals would be distorted by the electrical and/or electromagnetic interferences emanating from the MRI equipment. As a consequence, for such an environment and other environments whereby electrical interferences would prevent the telemetry of physiological signals measured from a patient by a remote oximeter or oximetry unit, another method of transmitting the signal for the instant invention would be by using fiber optics, in particular by means of a fiber optic cable that communicatively connects the remote oximeter to the on-site oximeter from which the readings of the physiological parameters measured from the patients are displayed. An output port may be provided at the remote oximetry for connection to the fiber optic cable, with the other end of the fiber optic cable being routed in a conventional manner to the room where the on-site oximeter is located. The end of the fiber optic cable that is to be connected to the on-site oximeter. By be fitted with a connector that readily mates with the built-in connector of the on-site oximeter. By transmitting the signal through glass fibers, the integrite of the signal is not affected by the electrical or electromagnetic interference generates from the MRI or other similar equipment.

What is claimed is:

1. Apparatus for providing remote measurement of oxygen saturation level of blood, comprising:
    an input for receiving a signal from a remote oximeter unit;
    simulator means for adapting the signal received from said remote oximeter unit for measurement by an on-site oximeter; and
    an output unit adapted to be fitted to a sensor of said on-site oximeter to provide an output based on the adapted signal.

2. Apparatus of claim 1, wherein said output unit comprises a body configured to fit to said sensor of said oximeter, said body having a light source and a light detector; and
    wherein when said body is fitted to said sensor, said light source of said body is aligned to be in opposed relationship with a photodetector of said sensor and said light detector of said body is aligned to be in opposed relationship with a light emitter of said sensor.

3. Apparatus of claim 1, wherein said simulator means comprises:
    processor means for receiving the signal from said remote oximeter unit, said processor means generating a number that corresponds to the received signal from said remote oximeter unit;
    photodetector means at said output unit positioned relative to a light emitter of said sensor of said oximeter for sensing light output from said light emitter and for outputting a second signal representative of the intensity of the sensed light output from said light emitter;
    comparator means for receiving the second signal output from said photodetector means, said comparator means outputting a third signal based on the received second signal to said processor means; and
    digital to analog converter means for receiving the second signal output from said photodetector means and the number from said processor means, said digital to analog converter means outputting a fourth signal in response to the second signal and said number to control the output of light from a light source at said output unit positioned relative to a photodetector of said sensor of said oximeter.

4. Apparatus of claim 3, wherein said fourth signal output from said digital to analog means comprises an output voltage signal and said light source comprises a light emitting diode, said apparatus further comprising:

voltage to current converter means for converting the output voltage signal to a current for controlling the operation of said light emitting diode.

5. Apparatus of claim 3, wherein said number generated by said processor means is representative of the blood flow of the patient being measured by said remote oximeter unit for determining the oxygen saturation of blood of the patient.

6. Apparatus of claim 3, wherein said digital to analog converter means (DAC), in receipt of the second signal from said photodetector means and the number from said processor means, outputs the fourth signal as an output voltage based on the following formula:

$$V_{out}=V_{in}*(N/M)$$

Where $V_{out}$ and $V_{in}$ are the output and input voltages, respectively, out of and into the DAC;
N=number clocked into DAC; and
M=resolution number selected from $2^8$ to $2^{24}$.

7. Apparatus of claim 1, further comprising:
a RF receiver for receiving said signal serially from said remote oximeter unit.

8. Apparatus of claim 1, wherein said remote oximeter unit is communicatively connected to said input of said apparatus by a fiber optic cable through which said signal traverses.

9. An adapter for use with an oximeter for enabling said oximeter to monitor the SpO2 (Oxygen Saturation Level of Blood) of a patient located remote from said adapter and being measured by an oximetry unit remote from said oximeter, comprising:
an input for receiving a signal from said remote oximetry unit;
a coupling unit adapted to be mated to said oximeter; and
a circuit module for converting the signal received from said oximetry unit into a corresponding number and generating an adapted signal based on said corresponding number for said oximeter.

10. Adapter of claim 9, wherein said coupling unit comprises a body configured to fit into a sensor of said oximeter, said body having a light source and a light detector, wherein when said body is fitted to said sensor, said light source of said body is aligned to be in opposed relationship with a photodetector of said sensor and said light detector of said body is aligned to be in opposed relationship with a light emitter of said sensor.

11. Adapter of claim 9, wherein said circuit module comprises:
processor means having said input for receiving the signal from said oximetry unit, said processor means generating a the number that corresponds to the received signal from said oximetry unit;
photodetector means at said coupling unit positioned relative to a light emitter of a sensor of said oximeter for sensing light output from said light emitter and for outputting a second signal representative of the intensity of the sensed light output from said light emitter;
comparator means for receiving the second signal output from said photodetector means, said comparator means outputting a third signal based on the received second signal to said processor means; and
digital to analog converter means for receiving the second signal output from said photodetector means and the number from said processor means, said digital to analog converter means outputting said adapted signal in response to the second signal and said number to control the output of light from a light source at said output unit positioned relative to a photodetector of said sensor of said oximeter.

12. Adapter of claim 9, wherein said coupling unit comprises a connector configured to mate with a counterpart connector at said oximeter.

13. Adapter of claim 9, wherein said circuit module comprises:
an input circuit in direct communication with the light emitter circuit of said oximeter for receiving a second signal representative of the light output from said oximeter;
an opto-coupler circuit in direct communication with the photodetector circuit of said oximeter;
a processor having an input for receiving the signal from said oximetry unit, said processor generating a number that corresponds to the received signal from said oximetry unit;
a comparator circuit for receiving the second signal from said input circuit, said comparator circuit outputting a third signal based on the received signal to said processor means; and
a digital to analog converter circuit for receiving the second signal from said input circuit and said number from said processor, said digital to analog converter circuit outputting said adapted signal in response to the second signal and said number to said photodetector circuit of said oximeter via said opto-coupler circuit.

14. Adapter of claim 13, wherein said adapted signal comprises an output voltage, said adapter further comprising:
a voltage to current converter circuit for converting the output voltage to an current for driving photo-diodes in said opto-coupler circuit, the outputs of said photo-diodes being fed to said photodetector circuit of said oximeter.

15. Adapter of claim 13, wherein said digital to analog converter circuit (DAC), in receipt of the second signal from said input circuit and the number from said processor, outputs said adapted signal as an output voltage based on the following formula:

$$V_{out}=V_{in}*(N/M)$$

Where $V_{out}$ and $V_{in}$ are the output and input voltages, respectively, out of and into the DAC;
N=number clocked into DAC; and
M=resolution number selected from $2^8$ to $2^{24}$.

16. Adapter of claim 13, wherein said input circuit comprises a loaded resistance rectifier circuit having dual diodes for receiving the second signal from the light emitting circuit of said oximeter.

17. Adapter of claim 9, wherein said remote oximetry unit outputs said signal to said input of said adapter via a fiber optic connection.

18. An adapter for use with an oximeter for enabling said oximeter to monitor the SpO2 (Oxygen Saturation Level of Blood) of a patient remotely located from said adapter and being measured by an oximetry unit remote from said oximeter, comprising:
a connection to a RF receiver for receiving a signal from said oximetry unit;
a connector adapted to be mated to a counterpart connector at said oximeter; and
a circuit module for converting the signal received from said oximetry unit into a corresponding number and generating an adapted signal based on said corresponding number for said oximeter.

19. Adapter of claim 18, wherein said circuit module comprises:
   an input circuit in communication via said connectors with the light emitter circuit of said oximeter for receiving a second signal representative of the light output from said oximeter;
   an opto-coupler circuit in communication via said connecters with the photodetector circuit of said oximeter;
   a processor for receiving the signal from said oximetry unit via said connection to said RF receiver, said processor generating the number that corresponds to the received signal from said oximetry unit;
   a comparator for receiving the second signal from said input circuit, said comparator outputting a third signal based on the received signal to said processor; and
   a digital to analog converter for receiving the second signal from said input circuit and said number from said processor, said digital to analog converter outputting said adapted signal in response to the second signal and said number to said photodetector circuit of said oximeter via said opto-coupler circuit.

20. Adapter of claim 19, wherein said adapted signal comprises an output voltage, said adapter further comprising:
   a voltage to current converter for converting the output voltage to an current for driving photo-diodes in said opto-coupler circuit, the outputs of said photo-diodes being fed to said photodetector circuit of said oximeter.

21. Adapter of claim 19, wherein said digital to analog converter (DAC), in receipt of the second signal from said input circuit and the number from said processor, outputs said adapted signal as an output voltage based on the following formula:

$$V_{out}=V_{in}*(N/M)$$

Where $V_{out}$ and $V_{in}$ are the output and input voltages, respectively, out of and into the DAC;
   N=number clocked into DAC; and
   M=resolution number selected from $2^8$ to $2^{24}$.

22. Adapter of claim 18, wherein said input circuit comprises a loaded resistance rectifier circuit having dual diodes for receiving the second signal from the light emitting circuit of said oximeter.

23. A method of enabling an oximeter to monitor the SpO2 (Oxygen Saturation Level of Blood) of a patient being measured by an oximetry unit remote from said oximeter, comprising the steps of:
   receiving a signal from said remote oximetry unit;
   converting the signal received from said oximetry unit into a corresponding number for said oximeter;
   and coupling a unit to said oximeter for transmitting an adapted signal generated based on said number to said oximeter.

24. Method of claim 23, wherein said coupling step comprises the steps of:
   configuring a body to fit into a sensor of said oximeter, said body having a light source and a light detector; and
   aligning said light source of said body to be in opposed relationship with a photodetector of said sensor and said light detector of said body to be in opposed relationship with a light emitter of said sensor when said body is fitted to said sensor.

25. Method of claim 23, wherein said adapting step comprises the steps of:
   inputting to a processor means the signal from said oximetry unit, said processor means generating said number that corresponds to the received signal from said oximetry unit;
   positioning a photodetector means relative to a light emitter of a sensor of said oximeter, said photodetector means sensing light output from said light emitter and outputting a second signal representative of the intensity of the sensed light output from said light emitter;
   inputting the second signal output from said photodetector means to a comparator means, said comparator means outputting a third signal based on the received second signal to said processor means; and
   inputting the second signal output from said photodetector means and the number from said processor means to a digital to analog converter means, said digital to analog converter means outputting said adapted signal in response to the second signal and said number to control the output of light from a light source at said output unit positioned relative to a photodetector of said sensor of said oximeter.

26. Method of claim 25, wherein said adapted signal output from said digital to analog means comprises an output voltage signal and said light source comprises a light emitting diode, said method further comprising the step of:
   converting the output voltage signal to a current for controlling the operation of said light emitting diode.

27. Method of claim 23, wherein said coupling step comprises the step of:
   configuring a connector to mate with a counterpart connector at said oximeter.

28. Method of claim 23, wherein said adapting step comprises the steps of:
   inputting to an input circuit in direct communication with the light emitter circuit of said oximeter a second signal representative of the light output from said oximeter;
   effecting an opto-coupler circuit in direct communication with the photodetector circuit of said oximeter;
   providing to a processor the signal from said oximetry unit, said processor generating a number that corresponds to the received signal from said oximetry unit;
   providing to the second signal from said input circuit to a comparator circuit, said comparator circuit outputting a third signal based on the received signal to said processor means; and
   providing to a digital to analog converter circuit the second signal from said input circuit and said number from said processor, said digital to analog converter circuit outputting said adapted signal in response to the second signal and said number to said photodetector circuit of said oximeter via said opto-coupler circuit.

29. Method of claim 28, wherein said adapted signal comprises an output voltage, said method further comprising the step of:
   converting the output voltage to an current for driving photo-diodes in said opto-coupler circuit, the outputs of said photo-diodes being fed to said photodetector circuit of said oximeter.

30. Method of claim 23, wherein said converting step comprises the steps of:
   inputting the signal from said oximetry unit as said number, said number being a representative number calculated from a processor and another signal received from a light emitting circuit of said oximeter to a digital to analog converter (DAC);

effecting said DAC to output an output voltage based on the following formula:

$$V_{out} = V_{in} * (N/M)$$

Where $V_{out}$ and $V_{in}$ are the output and input voltages, respectively, out of and into the DAC;

N=number clocked into DAC; and

M=resolution number selected from $2^8$ to $2^{24}$.

31. Method of claim 23, wherein said receiving a signal step further comprises the step of:

receiving said signal from said remote oximetry unit via a fiber optic cable connecting said remote oximetry unit and said oximeter.

* * * * *